(12) United States Patent
Cyr

(10) Patent No.: US 6,381,749 B1
(45) Date of Patent: May 7, 2002

(54) PROTECTIVE MASK WITH ANCHOR CLAMP FOR PHYSICAL GAMES

(75) Inventor: Raymond Cyr, Duvernay (CA)

(73) Assignee: Leader Industries Inc., Quebec (CA)

( * ) Notice: Subject to any disclaimer, the term of this patent is extended or adjusted under 35 U.S.C. 154(b) by 0 days.

(21) Appl. No.: 09/501,326

(22) Filed: Feb. 9, 2000

(51) Int. Cl.[7] .............................. A41D 13/00; A61F 9/02
(52) U.S. Cl. ........................... 2/9; 2/426; 2/427; 2/441; 2/443
(58) Field of Search .......................... 2/9, 10, 11, 15, 2/6.3, 6.7, 410, 411, 424, 425, 426, 427, 438, 441, 443

(56) References Cited

U.S. PATENT DOCUMENTS

| | | | | |
|---|---|---|---|---|
| 3,259,908 A | * | 7/1966 | Simpson et al. | 2/9 |
| 3,984,875 A | * | 10/1976 | Farquharson | 2/10 |
| 4,764,990 A | * | 8/1988 | Markert | 2/429 |
| 5,093,936 A | * | 3/1992 | Copeland et al. | 2/419 |
| 5,148,550 A | * | 9/1992 | Hodgkinson et al. | 2/424 |
| 5,412,814 A | * | 5/1995 | Pernicka et al. | 2/424 |

* cited by examiner

Primary Examiner—Michael A. Neas
(74) Attorney, Agent, or Firm—Fulbright & Jaworski

(57) ABSTRACT

A protective mask adapted to be worn by persons engaging in physical games comprises a body consisting of a lens receiving portion, a nose portion, a chin portion, a brow portion, opposite cheek portions and opposite side temple portions; the lens receiving portion displays an opening which is covered by a removable flexible transparent lens having its opposite extremities configured with engagement portions that mount the lens to the body. A pair of anchor clamps are inserted at each opposite end of the lens to further secure the engagement of the lens to the mask body.

9 Claims, 4 Drawing Sheets

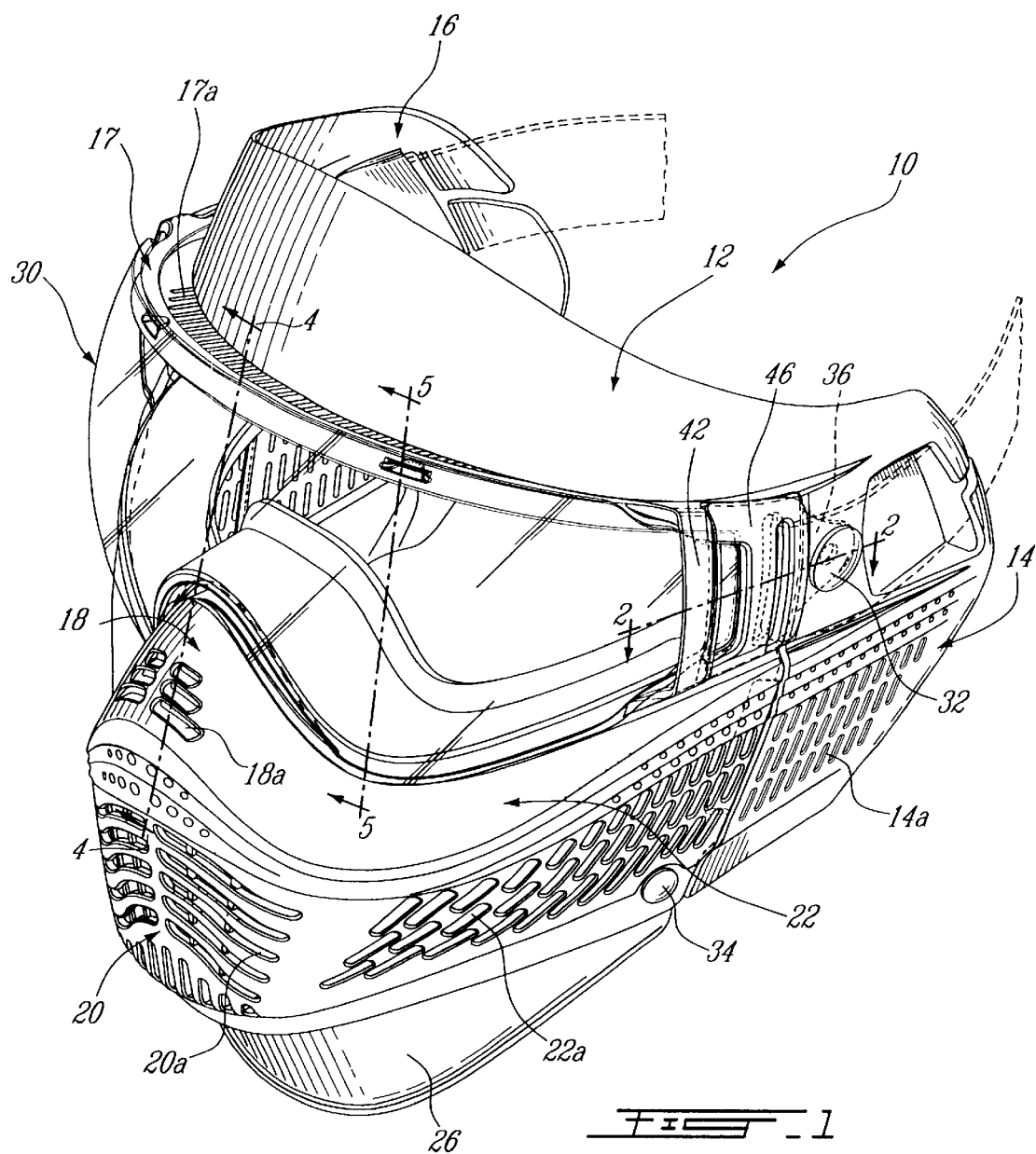

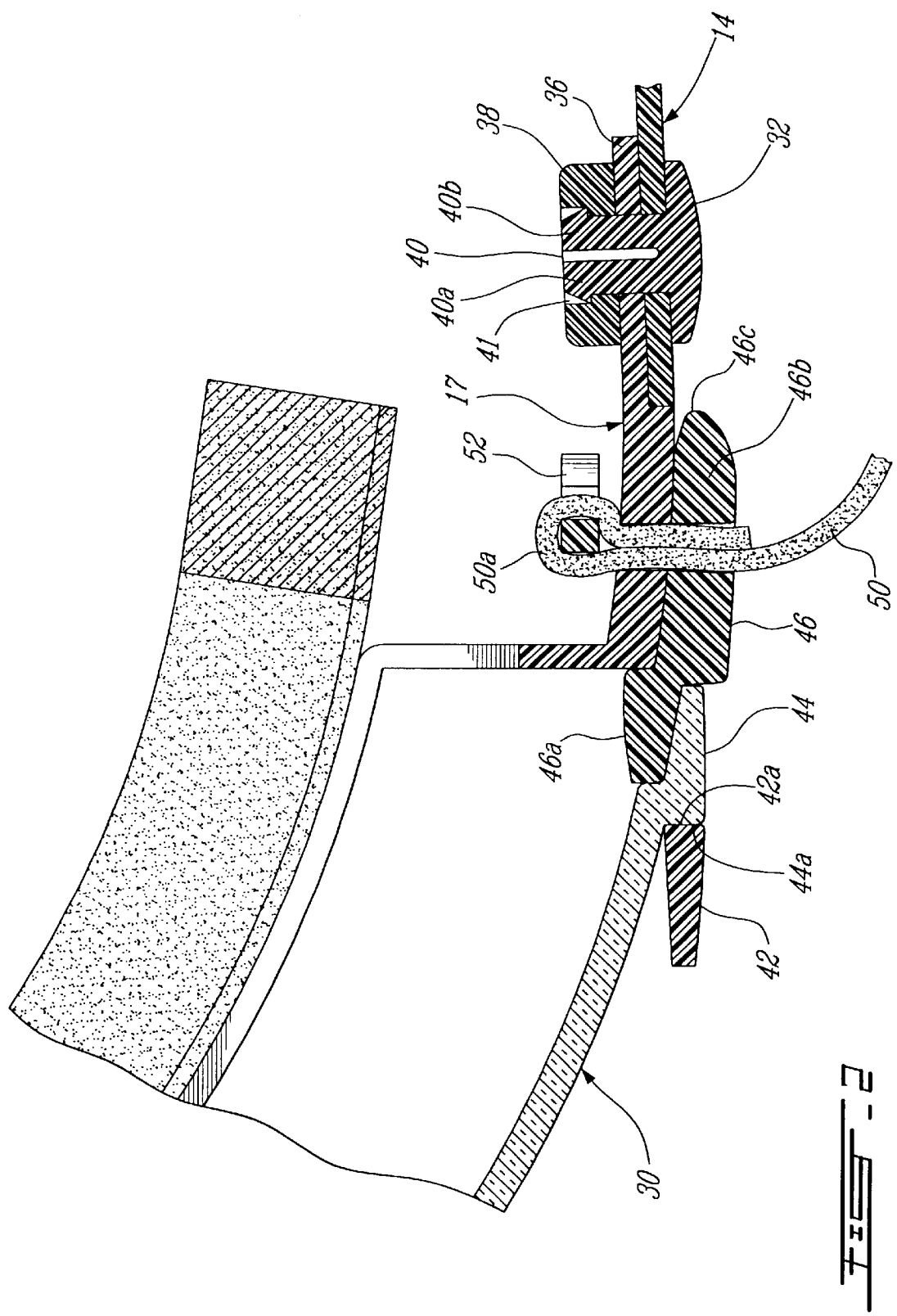

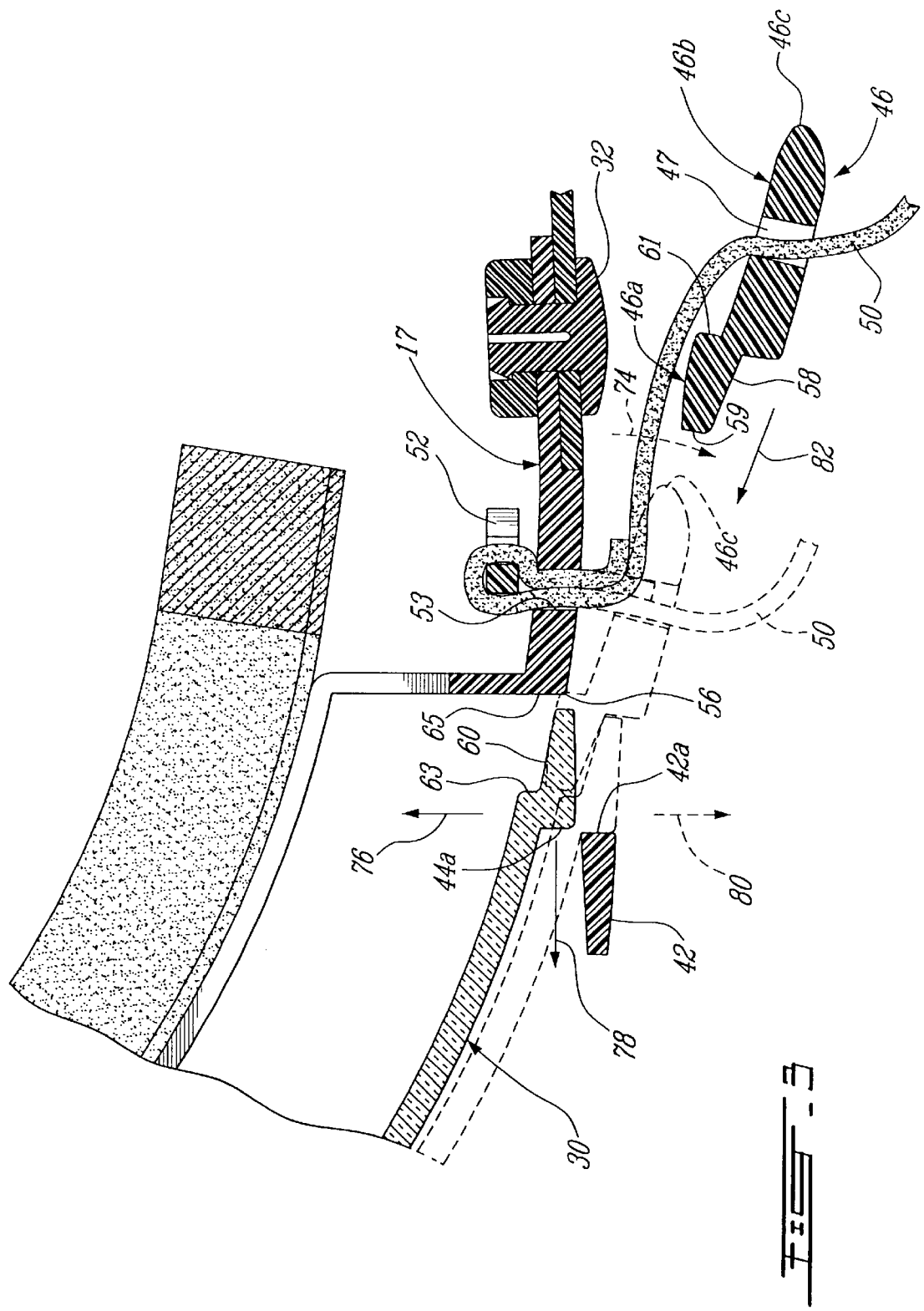

US 6,381,749 B1

PROTECTIVE MASK WITH ANCHOR CLAMP FOR PHYSICAL GAMES

FIELD OF THE INVENTION

The present invention pertains to a protective mask adapted to be worn by persons engaging in physical games.

BACKGROUND OF THE INVENTION

Protective masks are typically used in an environment in which flying objects or projectiles may be present. An example of such an environment is in the game of paint ball projectiles which are impacted onto players in order to display a hit. In order to protect the player's eyes, a lens assembly is used in association with a face mask in order to fully cover the front face and the sides of a player's head. The lens is preferably removable so that it can be easily replaced either for washing or for replacement should it be damaged. The lens is securely mounted to the face mask; however, due to the hard impact of the projectiles, the lens, in some cases, is accidently dislodged or disengaged from its securement to the mask, thus resulting in possible accidents to player during the game.

OBJECTS AND STATEMENT OF THE INVENTION

It is an object of the present invention to overcome the above described problem of accidental dislodgement of a lens from the face mask. This is achieved by providing an additional anchoring to further secure the inter-engaging sections of the lens and the face mask.

The present invention therefore relates to a protective mask which is adapted to be worn by persons engaging in physical games; it comprises:
  a main body formed of rigid plastic material; the body has a configuration to cover the front and sides of a person's head and includes a first part consisting of a brow portion and opposite side temple portions and a second part consisting of a lens receiving portion, a nose portion, a chin portion and opposite cheek portions; the lens receiving portion defines an opening and includes first engaging means adjacent each opposite side end of the opening;
  a removable flexible transparent lens adapted to engagedly cover the opening; the lens has, at each opposite side end, second engaging means adapted to snapingly engage the first engaging means; the lens is flexible in a direction enabling distance variation between the side ends thereof so that manual pressure exerted on the lens causes the lens to snapingly engage with or to disengage from the first engaging means; and
  removable anchor means mounted at each opposite side end of the lens receiving portion and insertable at the opposite side ends of the lens to further secure the first and second engaging means together in an engagement position.

In one form of the invention, the removable anchor means are shaped, on the one hand, to fittingly receive the ends of the lens and, on the other hand, with a slot to receive therethrough the strap that serves to mount the mask to the user's head.

Other objects and further scope of applicability of the present invention will become apparent from the detailed description given hereinafter. It should be understood, however, that this detailed description, while indicating preferred embodiments of the invention, is given by way of illustration only, since various changes and modifications within the spirit and scope of the invention will become apparent to those skilled in the art.

BRIEF DESCRIPTION OF THE DRAWINGS

FIG. 1 is a perspective view of a protective mask made in accordance with the present invention;

FIG. 2 is an enlarged cross-sectional view taken along lines 2—2 of FIG. 1;

FIG. 3 is a cross-sectional view similar to FIG. 2 showing the removal of the locking means;

DESCRIPTION OF PREFERRED EMBODIMENTS

Figure 5:
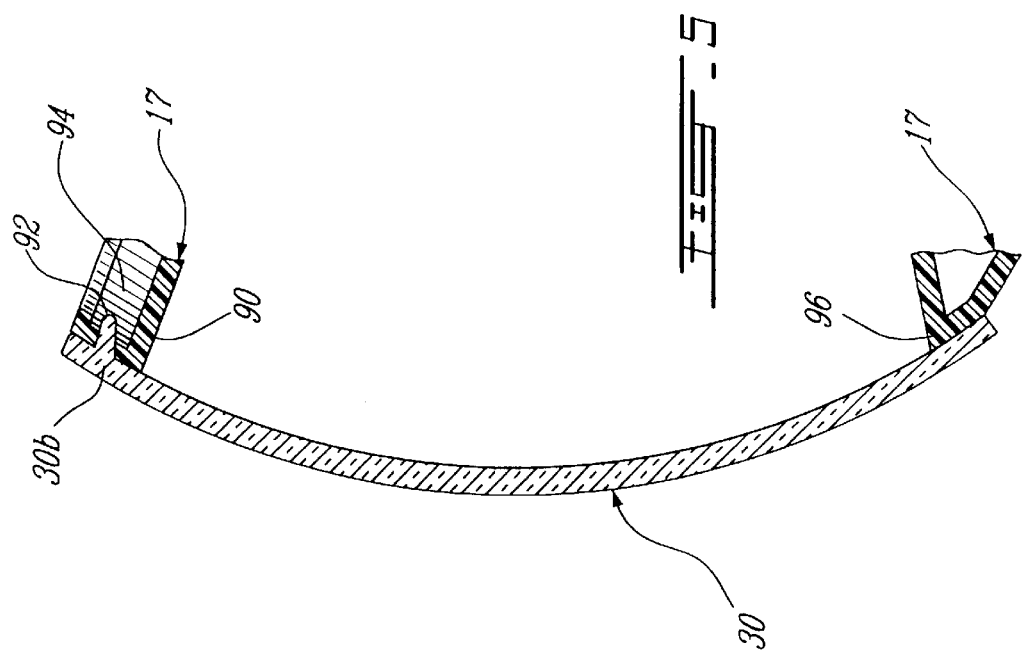
FIG. 5 is a cross-sectional view taken along lines 5—5 of FIG. 1.

Referring to FIG. 1, there is shown a protective mask, generally denoted 10, made in accordance with the present invention. The mask comprises a main body made of rigid plastic material consisting of a first part including a brow portion 12 integral with a pair of opposite side temple portions 14 and 16, and of a second part including a lens receiving portion 17, a nose portion 18, a chin portion 20 and opposite cheek portions 22.

A throat guard 26 is pivotally mounted to the lower part of the mask; this throat guard is described in details in a patent application filed concurrently herewith. The lens receiving, nose, chin and cheek portions are provided with a series of holes 17a, 18a, 20a, 22a to provide ventilation for the user's face. Similar ventilation holes 14a are provided on the side temple portions 14 and 16 and, although not shown, could also be provided on the brow portion 12.

An optically transparent lens 30 covers the opening formed in the lens receiving portion 17 of the mask and is made of flexible material so that it may be elastically deformed by manual pressure in a direction enabling distance variation between its side extremities.

A pair of fastening pins 32 and 34 is provided on each side of the mask to secure the first part to the second part. More particularly, and referring to FIG. 2, the lens receiving portion 17 has a pair of side extensions 36 that lies behind the side temple portions 14 and 16. An annular member 38 engages the split stem portion 40 of the pin 32 which protrudes through registered openings in the three elements 14, 36 and 38. Once the stem portion 40 is received in these openings, its two semi-circular segments 40a and 40b spring outwardly to snap into engagement with a shoulder in the pin recess 41.

Referring also to FIGS. 1 and 2, extending vertically at each opposite end of the lens opening is a frontwardly extending integral bridge or post portion 42 against which bears the lens extremity 44 having a L-shaped in cross-section. Referring further to FIG. 3, extremity 44 has an outer wall 44a that is configured to contact the rear wall 42a of the bridge portion 42. This contact is achieved by causing an inward flexing of the plastic lens, by inserting extremities 44 behind the bridge portions 42 and then by releasing the flexing so that the resiliency of the lens material will cause and maintain the inter-engagement of the lens to the face mask body.

The present invention is concerned with insuring that this contact is maintained; this is achieved by the provision of a pair of anchor clamps 46. As can be best seen in FIG. 3, the anchor clamps 46 have a front portion 46a which is shaped to receive the L-shaped extremity 44 of the lens and a rear portion 46b having an opening 47 to receive a strap 50 having a loop 50a to which is engaged a stop member 52. An opening 53 is also provided in the lens receiving portion 17 to allow the passage of the strap 50 therethrough.

FIG. 2 shows the position of anchor 46 in a clamping condition. The underface 58 of the locking member bears against the rear wall 60 of the lens while the front and rear faces 59 and 61 are held tight against face 63 of the lens and wall 65 of the lens receving portion 17 of the mask.

FIG. 3 shows how the removal of the anchor clamp 46 is achieved. The user uses its finger to engage the extremity 46c to pivot the locking member in the direction indicated by arrow 74 about the corner 56 of the lens receiving portion 17. This will free the contact between surfaces 58 and 59 of the anchor clamp 46 and surfaces 60 and 63 of the extremity 44 of the lens. Then, to remove the lens 30, manual pressure is exerted on the lens in the direction indicated by arrow 76; and, in the direction indicated by arrow 78, the extremity 44 of the lens is frontwardly distanced from the bridge portion 42. Inversely, the insertion of the anchor clamp 46 is accomplished by first positionning the extremity 44 of the lens in the direction indicated by arrow 80 (as explained above) and subsequently inserting the anchor clamp 46 as indicated by arrow 82 between the lens extremity 44 and the portion 17 so that surfaces 58 and 59 may engage surfaces 60 and 63; then, by pushing portion 46b of the anchor clamp in a direction opposite to the direction 74, the interengagement of the lens with the face mask 42 is further secured.

Figure 4:
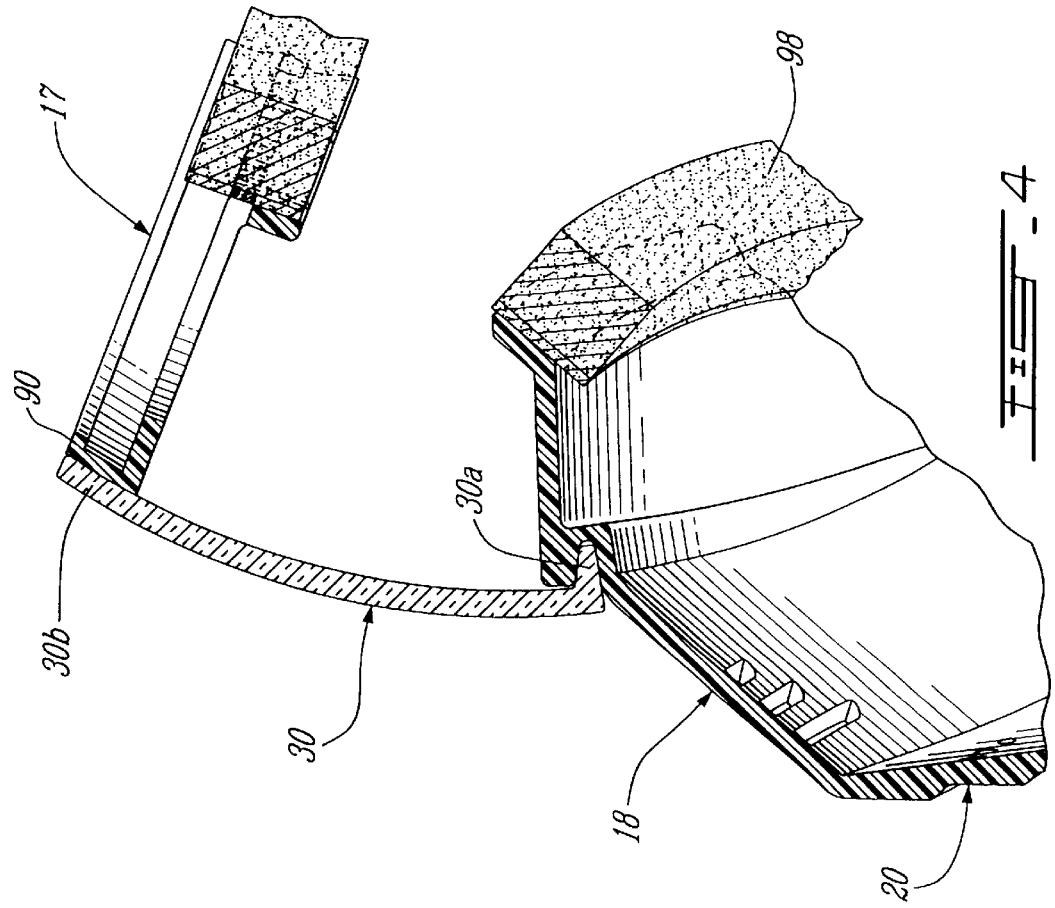
FIG. 4 is a cross-sectional view taken along lines 4—4 of FIG. 1.

Referring to FIGS. 4 and 5, the lens 30 has, in the nose region, an inward edge 30a that fits into a correspondingly shaped slot that follows the contour of the nose portion 18 while the upper edge 30b bears against an upper border 90 of the lens receiving portion 17 of the mask body. This upper border 30b of the lens comprises a series of inwardly projecting pins or tongues 92 that fit into correspondingly shaped openings 94 in the upper border 90 while the lower border 30a of the lens bears against the border 96 of the lens receiving portion 17.

A protective padding 98 is shown in FIG. 4 on the inner side of the mask along the borders of the opening to soften any blows received on the mask and transmitted to the player's face during the game.

Although the invention has been described above with respect to one specific form, it is evident that it may be varied and refined in various ways. For example, the mask could be modified to suit other physical games, such as ice hockey or sports, such as moto-cross, motorcycling, where protection is required, where the replacement of a protective lens is needed or where hard impact on the lens may cause its dislodgement from its actual engagement to main body of the mask. It is therefore wished to have it understood that the present invention should not be limited in scope, except by the terms of the following claims.

What is claimed is:

1. A protective mask adapted to be worn by persons engaging in physical games comprising:
    a main body formed of rigid plastic material: said body having a configuration to cover the front and sides of a person's head and including a first part consisting of a brow portion and opposite side temple portions and a second part consisting of a lens receiving portion, a nose portion, a chin portion, and opposite cheek portions; said lens receiving portion defining a lens opening and including first engaging means adjacent each opposite side end of said opening:
    a removable flexible transparent lens adapted to engagedly cover said opening; said lens having, at each opposite side end, second engaging means adapted to snapingly engage said first engaging means; said lens being flexible in a direction enabling distance variation between said side ends thereof so that manual pressure exerted on said lens causes said lens to snapingly engage with or to disengage from said first engaging means; and
    removable anchor means mounted at each said opposite side end of said lens receiving portion and insertable at said opposite side ends of said lens to further secure said first and second engaging means together in an engagement position,
    wherein each said anchor means includes a first portion shaped to receive said side end of said lens and to bear against said first engaging means, and a second portion consisting of a slot to receive a strap there through for mounting said mask to a person's head.

2. A protective mask as defined in claim 1, wherein an opposite end of said first part adjacent said lens opening comprises a strap receiving slot adapted to come into registry with said slot of said second portion of said anchor means when said anchor means are mounted to said first part of said body and said lens.

3. A protective mask adapted to be worn by persons engaging in physical games comprising:
    a main body formed of rigid plastic material: said body having a configuration to cover the front and sides of a person's head and including a first part consisting of a brow portion and opposite side temple portions and a second part consisting of a lens receiving portion, a nose portion, a chin portion, and opposite cheek portions; said lens receiving portion defining a lens opening and including first engaging means adjacent each opposite side end of said opening:
    a removable flexible transparent lens adapted to engagedly cover said opening; said lens having, at each opposite side end, second engaging means adapted to snapingly engage said first engaging means; said lens being flexible in a direction enabling distance variation between said side ends thereof so that manual pressure exerted on said lens causes said lens to snapingly engage with or to disengage from said first engaging means; and
    removable anchor means mounted at each said opposite side end of said lens receiving portion and insertable at said opposite side ends of said lens to further secure said first and second engaging means together in an engagement position,
    comprising fastening means for securing said first part of said main body to said second part of said body.

4. A protective mask adapted to be worn by persons engaging in physical games comprising:
    a main body formed of rigid plastic material: said body having a configuration to cover the front and sides of a person's head and including a first part consisting of a brow portion and opposite side temple portions and a second part consisting of a lens receiving portion, a nose portion, a chin portion, and opposite cheek portions; said lens receiving portion defining a lens opening and including first engaging means adjacent each opposite side end of said opening:
    a removable flexible transparent lens adapted to engagedly cover said opening; said lens having, at each opposite side end, second engaging means adapted to snapingly engage said first engaging means; said lens being flexible in a direction enabling distance variation between said side ends thereof so that manual pressure exerted on said lens causes said lens to snapingly engage with or to disengage from said first engaging means; and removable anchor means mounted at each said opposite side end of said lens receiving portion and insertable at said opposite side ends of said lens to further secure said first and second engaging means together in an engagement position, wherein said lens include a series of projections along an upper edge thereof to engage cooperating openings in said first part of said main body.

5. A protective mask adapted to be worn by persons engaging in physical games comprising:

a main body formed of rigid plastic material: said body having a configuration to cover the front and sides of a person's head and including a first part consisting of a brow portion and opposite side temple portions and a second part consisting of a lens receiving portion, a nose portion, a chin portion, and opposite cheek portions; said lens receiving portion defining a lens opening and including first engaging means adjacent each opposite side end of said opening:

a removable flexible transparent lens adapted to engagedly cover said opening; said lens having, at each opposite side end, second engaging means adapted to snapingly engage said first engaging means; said lens being flexible in a direction enabling distance variation between said side ends thereof so that manual pressure exerted on said lens causes said lens to snapingly engage with or to disengage from said first engaging means; and removable anchor means mounted at each said opposite side end of said lens receiving portion and insertable at said opposite side ends of said lens to further secure said first and second engaging means together in an engagement position, each said anchor means including a first portion shaped to receive said side end of said lens when said anchor means is slid into engagement thereby forcing said second engaging means on said lens to bear against said first engaging means of said body.

6. A protective mask as defined in claim 5, comprising pad means fixed to an inner side of said main body adjacent a border of said lens opening.

7. A protective mask as defined in claim 5, wherein said nose, chin and cheek portions display ventilation openings.

8. A protective mask as defined in claim 5, further comprising a throat protective guard pivotally mounted to the lower part of said cheek portions.

9. A protective mask as defined in claim 5, wherein said second part of said body comprising ventilation openings.

* * * * *